United States Patent [19]

Cullinan

[11] Patent Number: 5,043,340

[45] Date of Patent: Aug. 27, 1991

[54] DERIVATIVES OF 4-DESACETYL VLB C-3 CARBOXHYDRAZIDE

[75] Inventor: George J. Cullinan, Trafalgar, Ind.

[73] Assignee: Eli Lilly and Company, Indianapolis, Ind.

[21] Appl. No.: 503,636

[22] Filed: Apr. 3, 1990

[51] Int. Cl.$^5$ ............... A61K 31/475; A61K 31/395; C07D 519/04; C07K 15/28

[52] U.S. Cl. .................................. 514/283; 540/478; 530/391; 530/809; 530/806; 530/828; 424/85.91

[58] Field of Search ............... 540/478; 514/283, 212, 514/218

[56] References Cited

U.S. PATENT DOCUMENTS

| | | | |
|---|---|---|---|
| 4,166,810 | 9/1979 | Cullinan et al. | 540/478 |
| 4,191,688 | 3/1980 | Conrad et al. | 540/478 |
| 4,203,898 | 5/1980 | Cullinan et al. | 540/478 |
| 4,388,305 | 6/1983 | Trouet et al. | 514/283 |
| 4,596,676 | 6/1986 | Cullinan | 540/478 |
| 4,675,400 | 6/1987 | Cullinan | 540/478 |
| 4,801,688 | 1/1989 | Laguzza et al. | 530/391 |

FOREIGN PATENT DOCUMENTS 056322 of 0000 European Pat. Off. .
0243929 of 0000 European Pat. Off. .

OTHER PUBLICATIONS

Ghose et al., CRC Crit. Rev. in Therapeutic Drug Carrier Systems, 3, 263–359 (1987).

Blair and Ghose, *J. Immunol. Methods*, 59, 129–43 (1983).

Ghose et al., *Methods Enzymol.* 93, 280–333 (1983).

*Primary Examiner*—Diana Rivers
*Attorney, Agent, or Firm*—Joseph A. Jones; Leroy Whitaker

[57] ABSTRACT

Derivatives of 4-desacetyl VLB C-3 carboxhydrazide, active anti-tumor agents and useful as intermediates for active anti-tumor conjugates.

18 Claims, No Drawings

DERIVATIVES OF 4-DESACETYL VLB C-3 CARBOXHYDRAZIDE

BACKGROUND OF THE INVENTION

Several naturally-occurring alkaloids obtainable from Vinca rosea have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leuroformine (Belgian Pat. No. 811,110); leurosidine (vinrosidine) and leurocristine (to be referred to hereafter as vincristine) (both in U.S. Pat. No. 3,205,220); deoxy VLB "A" and "B", Tetrahedron Letters, 783 (1958); 4-desacetoxyvinblastine (U.S Pat. No. 3,954,773; 4-desacetoxy-3'-hydroxyvinblastine (U.S. Pat. No. 3,944,554); leurocolombine (U.S. Pat. No. 3,890,325) and vincadioline (U.S. Pat. No. 3,887,565). Two of these alkaloids, VLB and vincristine, are now marketed as drugs for the treatment of malignancies, particularly the leukemias and related diseases in humans. The two marketed alkaloids are customarily administered by the i.v. route.

Chemical modification of the Vinca alkaloids has been rather limited. In the first place, the molecular structures involved are extremely complex, and chemical reactions which modify one specific functional group of the molecule without affecting other groups are difficult to develop. Secondly, dimeric alkaloids lacking desirable chemotherapeutic properties have been recovered or produced from Vinca rosea fractions or alkaloids, and a determination of their structures has led to the conclusion that these "inactive" compounds are closely related to the active alkaloids, frequently differing only as to stereochemistry at a single carbon. Thus, anti-neoplastic activity seems to be limited to very specific basic structures, and the chances of obtaining more active drugs by modification of these structures would seem to be correspondingly slight. Among the successful modifications of physiologically-active alkaloids has been the preparation of 6,7-dihydro VLB (U.S. Pat. No. 3,352,868) and the replacement of the acetyl group at C-4 (carbon no. 4 of the VLB ring system—see the numbered structure below) with higher alkanoyl group or with unrelated acyl groups. (See U.S. Pat. No. 3,392,173). Several of these C-4 derivatives are capable of prolonging the life of mice inoculated with P1534 leukemia. One of the C-4 derivatives in which a chloroacetyl group replaces the C-4 acetyl group of VLB is also a useful intermediate for the preparation of structurally modified VLB compounds in which an N,N-dialkylglycyl group replaces the C-4 acetyl group of VLB (See U.S. Pat. No. 3,387,001). C-3 carboxamide and carboxhydrazide derivatives of VLB, vincristine, vincadioline etc. have also been prepared and found to be active anti-tumor agents. (Belgian Pat. No. 813,168). These compounds are extremely interesting because, for example, the 3-carboxamides of VLB are more active against Ridgeway osteogenic sarcoma and Gardner lymphosarcoma than is VLB itself, the basic alkaloid from which they are derived. Certain of these amide derivatives actually approach the activity of vincristine against the same tumors. One of the amides, 4-desacetyl VLB C-3 carboxamide or vindesine, is currently being marketed for the treatment of malignancies, particularly in leukemias and related diseases. In humans, vindesine appears to have less neurotoxicity than does vincristine and is apparently effective against vincristine-resistant leukemias.

4-desacetyl VLB C-3 carboxhydrazide is disclosed in Belgian Pat. No. 813,168 as being an active anti-tumor agent against transplanted tumors in mice. It has been shown to be active against Ridgeway osteogenic sarcoma, Gardner lymphosarcoma and P 1534(J) leukemia The science of pharmaceutical chemistry has progressively provided more and more specific and potent drugs for the treatment and prevention of illness. However, until quite recently, there has been no means to direct a drug to the specific part of the body where it is needed. Thus, although it is often possible to treat a patient with a drug which has the specific effect which is needed, and no other effect on the body, it is still necessary to administer a whole-body dose. On the other hand, if it were possible to direct a drug to the organ, tissue or even cell in need of the treatment, it would often be possible to administer an extremely small total dose, since the drug would concentrate itself where it is needed. The advantage in safety to the patient and economy of drug is obvious.

For some years now, the science of immunology has been attempting to provide such targeted treatments, by conjugating drugs with antibodies which are directed to specific antigens associated with the locations where the drug is needed. Patents and scientific articles concerning such antibody-drug conjugates have been published. However, up to the present time, no antibody-drug conjugate is approved for therapeutic use.

SUMMARY OF THE INVENTION

This invention provides compounds of the formula

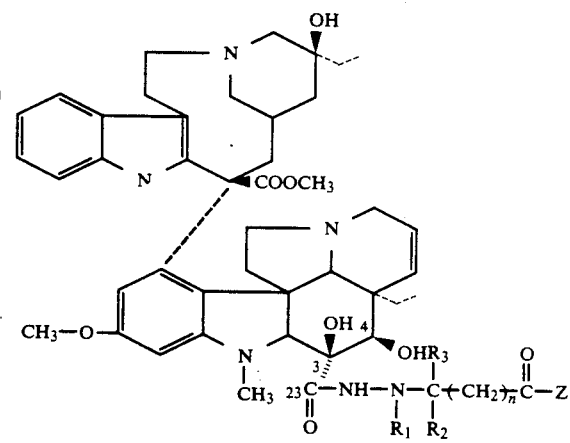

wherein
$R_1$ is hydrogen or taken together with $R_2$ to form a direct bond;
$R_2$ is hydrogen or taken together with $R_1$ to form a direct bond;
$R_3$ is hydrogen or methyl;
n is 2–4;
Z is Z' or Z" wherein Z' is hydroxy, $C_1$–$C_3$ alkoxy, or a carboxylic acid activating group;
Z" is —NH(CH$_2$)$_{n'}$·CO—Z';
n' is 1–3;
or a pharmaceutically acceptable salt thereof.

This invention also provides conjugates of the compounds of Formula I represented by the formula

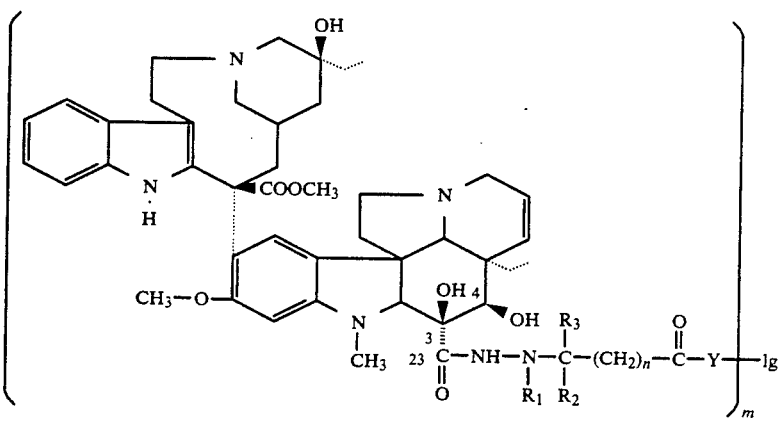

wherein
R$_1$, R$_2$, R$_3$, and n have their previous meaning;
Y is Y' or Y" wherein Y' is a direct bond to an amino group on the immunoglobulin or immunoglobulin fragment;
Y" is —NH(CH$_2$)$_{n'}$CO—Y';
n' is 1–3;
m is 1–10; and
Ig is an immunoglobulin or a fragment thereof, which recognizes an antigen associated with an undesirable cell.

The invention also provides a method of treating cancer or of controlling the growth of undesirable cells by administering a compound or a conjugate of the invention parenterally to the patient. A further aspect of the invention is a pharmaceutical therapeutic composition comprising a compound or a conjugate of the invention dispersed in a parenterally administrable medium.

In the above formula, when R$_1$ and R$_2$ are taken together to form a direct bond, the side chain is considered to be a Schiff's base. When R$_1$ and R$_2$ are hydrogen the side chain is considered to be a reduced Schiff's base. In the above formula, C$_1$–C$_3$ alkoxy refers to straight chain alkoxy groups such as methoxy, ethoxy, and propoxy but preferably methoxy.

The term, a carboxylic acid activating group, includes groups used in synthetic organic chemistry to increase the reactivity of a carboxylic acid. Such groups are frequently used by synthetic chemists, and include groups such as benzenesulfonyloxy, methanesulfonyloxy, toluenesulfonyloxy, phthalimidyloxy, succinimidyloxy, chloro, benzotriazolyloxy, bromo, azido and the like. The preferred activating groups in the present invention are N-succinimidyloxy, phthalimidyloxy and benzotriazolyloxy.

Pharmaceutically acceptable salts of Formula I include salts derived from inorganic acids or bases such as hydrochloric acid, nitric acid, phosphoric acid, sulfuric acid, hydrobromic acid, nitrous acid, phosphorous acid, sodium hydroxide, potassium hydroxide, calcium hydroxide and the like. Such pharmaceutically acceptable salts thus include the sulfate, pyrosulfate, bisulfate, sulfite, bisulfite, nitrate, phosphate, monohydrogenphosphate, dihydrogenphosphate, metaphosphate, pyrophosphate, chloride, bromide, iodide, sodium, potassium, calcium and the like.

DETAILED DESCRIPTION OF THE INVENTION

This invention provides novel 4-desacetyl VLB C-3 carboxhydrazide compounds which are useful as antitumor agents and as intermediates for anti-tumor protein conjugates Examples of the above defined 4-desacetyl VLB C-3 carboxhydrazide derivatives are described below in Table 1 wherein the terms in the column headings refer to Formula I.

TABLE 1

| R$_1$ | R$_2$ | R$_3$ | n | Z |
|---|---|---|---|---|
| H | H | H | 2 | —OH |
| Bond | | H | 3 | —OCH$_3$ |
| H | H | CH$_3$ | 4 | —OCH$_2$CH$_3$ |
| Bond | | CH$_3$ | 2 | —OCH$_2$CH$_2$CH$_3$ |
| H | H | H | 3 | —F |
| Bond | | H | 4 | —Cl |
| H | H | CH$_3$ | 2 | —Br |
| Bond | | CH$_3$ | 3 | —I |
| H | H | H | 4 | —N$_3$ |
| Bond | | H | 2 | —NHCH$_2$COOH |
| H | H | H | 3 | —NHCH$_2$CH$_2$COOCH$_3$ |
| Bond | | CH$_3$ | 4 | —NHCH$_2$CH$_2$CH$_2$COOCH$_2$CH$_3$ |
| H | H | CH$_3$ | 2 | —NHCH$_2$CH$_2$COOCH$_2$CH$_2$CH$_3$ |
| Bond | | CH$_3$ | 3 | —NHCH$_2$COF |
| H | H | H | 4 | —NHCH$_2$CH$_2$COCl |
| Bond | | H | 2 | —NHCH$_2$CH$_2$CH$_2$COBr |
| H | H | CH$_3$ | 3 | —NHCH$_2$CH$_2$COI |
| Bond | | CH$_3$ | 4 | —NHCH$_2$CON$_3$ |
| H | H | H | 2 | ![imidazole] —O—N |
| Bond | | H | 3 | —O—S(=O)$_2$—CH$_3$ |
| H | H | H | 3 | —O—S(=O)$_2$—C$_6$H$_4$—CH$_3$ |
| Bond | | CH$_3$ | 4 | —O—S(=O)$_2$—C$_6$H$_5$ |

TABLE 1-continued

| $R_1$ | $R_2$ | $R_3$ | n | Z |
|---|---|---|---|---|
| H | H | H | 2 | —O—N(succinimide-like ring with two C=O, attached to N) |
| Bond | CH$_3$ | | 3 | —O—N(phthalimide ring) |
| H | H | CH$_3$ | 4 | —O—N(benzotriazole) |
| Bond | H | | 2 | —NHCH$_2$CH$_2$COO—N(imidazole-type ring) |
| H | H | H | 3 | —NHCH$_2$CH$_2$CH$_2$COO—S(=O)$_2$—CH$_3$ |
| Bond | H | | 3 | —NHCH$_2$CH$_2$COOS(=O)$_2$—C$_6$H$_4$—CH$_3$ |
| H | H | CH$_3$ | 4 | —NHCH$_2$COO—N(imidazole-type ring with two C=O) |
| Bond | CH$_3$ | | 2 | —NHCH$_2$CH$_2$COO—N(phthalimide ring) |
| H | H | CH$_3$ | 3 | —NHCH$_2$CH$_2$CH$_2$COO—N(benzotriazole) |

The immunoglobulin material is an antibody or a fragment of an antibody adapted for recognition of antigens on the surface of unwanted cells.

Techniques for the production of such immunoglobulins from the serum of immunized animals or by culturing hybridomas secreting monoclonal products are well known. The preferred type of antibody for use in the invention is an immunoglobulin which is a gamma-globulin. IgG, IgA, IgE, and IgM subclasses are particularly preferred. Some representative immunoglobulins are as follows, mono- or polyclonal antibodies to
(i) human or animal tumor associated antigens;
(ii) human B- and T-cell antigens;
(iii) human Ia antigens;
(iv) viral, fungal and bacterial antigens; and
(v) cells involved in human inflammatory or allergic reactions.

Of the preferred antibodies to human or animal tumor associated antigens there may be mentioned:
  (i) Ig from goats or sheep immunized with carcinoembryonic antigen;
  (ii) Ig from rabbit antiacute lymphoblastic leukemia serum;
  (iii) Ig from various primate antisera raised against acute lymphoblastic leukemia, acute myleoblastic leukemia, chronic lymphoblastic leukemia and chronic granulocytic leukemia;
  (iv) Ig from goats or sheep immunized with lung carcinoma cells, or cellular fractions;
  (v) monoclonal Ig from mouse hybridomas secreting anti-human colorectal carcinoma antibodies;
  (vi) monoclonal Ig from mouse hybridomas secreting anti-human melanoma antibodies;
  (vii) monoclonal Ig from mouse hybridomas that secrete antibodies reacting with human leukemia cells;
  (viii) monoclonal Ig from mouse hybridomas secreting antibodies reacting with human neuroblastoma cells;
  (ix) monoclonal Ig from mouse hybridomas secreting antibodies reacting with human breast cancer antigens;
  (x) monoclonal Ig from mouse hybridomas secreting antibodies reacting with human ovarian carcinoma cells;
  (xi) monoclonal Ig from mouse hybridomas secreting antibodies reacting with human osteosarcoma cells, with human pancreatic carcinoma cells, with human prostatic carcinoma cells etc.;
  (xii) monoclonal Ig from mouse hybridomas secreting antibodies to adenocarcinomas including lung, renal, breast and pancreas;
  (xiii) monoclonal Ig from mouse hybridomas secreting antibodies reacting with human squamous carcinoma cells;
  (xiv) monoclonal Ig from human hybridomas (hybridomas which secrete antibodies to the human tumor-associated antigen including, but not limited to, those monoclonals above);
  (xv) chimeric Ig with mouse hypervariable regions and human constant regions;
  (xvi) monoclonal Ig from rat, hamster, or other mammalian species not specifically mentioned above, from hybridomas which secrete antibodies to human tumor associated antigens including, but not limited to, those mentioned above.

As indicated above, the conjugate can also be made with immunoglobulin fragments Ig', referred to also as Fab, Fab', F(ab')$_2$ and IgM monomer derived from an antibody by, for example, proteolytic enzyme digestion or reductive alkylation. Such materials and methods of preparation are well known and it may be mentioned that preferred proteolytic enzymes are pepsin and papain. See generally Parham, *J. Immunology*, 131, 2895 (1983); Lamoyi et al., *J. Immunological Methods*, 56, 235 (1983); Parham, id., 53, 133 (1982); and Matthew et al., id., 50,239 (1982).

Specific MoAbs exist that are reactive against various tumors; such immunoglobulins which recognize antigens on the surface of, or otherwise associated with tumor cells, include but are not limited to the following:

TABLE 2

| Tumor | MoAb | Reference |
|---|---|---|
| Lung | KS¼ | N. m. Varki, et al., Cancer Res. 44:681, 1984 |
|  | 534, F8; 604A9 | F. Cuttitta, et al., in: G. L. Wright (ed) Monoclonal Antibodies and Cancer, Marcel Dekker, Inc., N.Y., p. 161, 1984. |
| Squamous Lung Cancer | G1, LuCa2, LuCa3, LuCa4 | Kyoizumi et al., Cancer Res., 45:3274, 1985 |
| Small Cell Lung Cancer | TFS-2 | Okabe et al., Cancer Res. 45:1930, 1985 |
| Colon | 11.285.14 14.95.55 | G. Rowland, et al., Cancer Immunol. Immunother., 19:1, 1985. |
|  | NS-3a-22, NS-10 NS-19-9, NS-33a NS-52a, 17-1A | Z. Steplewski, et al., Cancer Res., 41:2723, 1981. |
| Melanoma | 9.2.27 | T. F. Bumol and R. A. Reisfeld, Proc. Natl. Acad. Sci., (U.S.A.), 79:1245, 1982 |
|  | p97 | K. E. Hellstrom, et al., Monoclonal Antibodies and Cancer, loc. cit. p. 31. |
|  | R24 | W. G. Dippold, et al., Proc. Natl. Acad. Sci. (U.S.A.), 77:6114, 1980. |
| Neuro-blastoma | Pl 153/3 | R. H. Kennet and F. Gilbert, Science, 203:1120, 1979. |
|  | MIN 1 | J. T. Kemshead in Monoclonal Antibodies and Cancer, loc. cit. p. 49. |
|  | UJ13A | Goldman et al., Pediatrics, 105:252, 1984. |
| Glioma | BF7, GE2, CG12 | N. de Tribolet, et al., in Monoclonal Antibodies and Cancer, loc. cit. p. 81. |
| Breast | B6.2, B72.3 | D. Colcher, et al., in Monoclonal Antibodies and Cancer, loc. cit. p. 121. |
| Osteogenic Sarcoma | 791T/48, 791T/36 | M. J. Embleton, ibid, p. 181 |
| Leukemia | CALL 2 | C. T. Teng, et al., Lancet, 1:01, 1982. |
|  | anti-idiotype | R. A. Miller, et al., N. Eng. J. Med., 306:517, 1982. |
| Ovary | OC 125 | R. C. Bast, et al., J. Clin. Invest., 68:1331, 1981. |
| Prostate | D83.21, P6.2, Turp-27 | J. J. Starling, et al., in Monoclonal Antibodies and Cancer, loc. cit. p. 253. |
| Renal | A6H, D5D | P. H. Lange, et al., Surgery, 98:143, 1985. |

Preferred conjugates are those prepared from monoclonal antibodies, especially those which recognize human cancer cells such as adenocarcinoma, squamous cell carcinoma, transitional cell carcinoma, melanoma, neuroblastoma, small cell carcinoma, leukemia, lymphoma, and sarcoma.

A preferred group of the 4-desacetyl VLB C-3 carboxyhydrazide compounds is represented by the Formula I wherein $R_1$ and $R_2$ are hydrogen.

Another preferred group is represented by the Formula I wherein $R_1$ and $R_2$ are taken together to form a direct bond.

A further preferred group is represented by the Formula I wherein $R_3$ is methyl.

A particularly preferred group is represented by the Formula I wherein Z is Z'.

A more particularly preferred group is represented by the Formula I wherein Z is Z" and n' is 2.

A further particularly preferred group is represented by the Formula I wherein Z' is hydroxy or a carboxylic acid activating group.

A more further particularly preferred group is represented by the Formula I wherein E' is N-succinimidyloxy, phthalimidyloxy or benzotriazolyloxy.

Preferred compounds represented by Formula I are those which are formed by choosing substituents for $R_1$, $R_2$, $R_3$, n' and Z from the preferred groups represented above.

A preferred group of the 4-desacetyl VLB C-3 carboxyhydrazide conjugates is represented by the Formula II wherein $R_1$ and $R_2$ are hydrogen.

Another preferred group is represented by the Formula II wherein $R_1$ and $R_2$ are taken together to form a direct bond.

A further preferred group is represented by the Formula II wherein $R_3$ is methyl.

A particularly preferred group is represented by the Formula II wherein Y is Y" and n' is 2.

Another particularly preferred group is represented by the Formula II wherein m is 1 to 8.

A further particularly preferred group is represented by the Formula II wherein Ig is a monoclonal antibody or fragment thereof which recognizes human cancer cells such as adenocarcinoma, squamous cell carcinoma, transitional cell carcinoma, melanoma, neuroblastoma, small cell carcinoma, leukemia, lymphoma, or sarcoma.

Preferred conjugates represented by Formula II are those which are formed by choosing substituents for $R_1$, $R_2$, $R_3$, Y, m, n' and Ig from the preferred groups represented above.

The compounds of this invention have been named as derivatives of 4-desacetyl VLB C-3 carboxyhydrazide. Systematic naming of these compounds should include a "3-descarbomethoxy" term but this term has been omitted since it is implicit in the name "C-3 carboxyhydrazide" in that the C-3 carbomethoxy group of VLB has been replaced. Additionally, an alternative naming system could have been employed; e.g., the compounds may be named as derivatives of 4-desacetyl VLB 23-desmethoxy-23-hydrazide referring to the replacement of the C-23 methoxy by hydrazide. However, in this specification it is prefered to name the compounds as C-3 carboxyhydrazide derivatives.

Hydrazine contains two nitrogen atoms, which are numbered in a hydrazide as follows

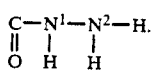

The hydrazide derivatives of this invention are all $N^2$ derivatives.

The compounds of this invention can be prepared by several alternative procedures. The preferred procedure involves the preparation first of 4-desacetyl VLB C-3 carboxhydrazide formed by the action of anhydrous hydrazine on VLB in a heated reaction vessel employing methanol as a solvent. The reaction of hydrazine with VLB itself serves to hydrolyze the acetoxy group at C-4 and thus the product of the reaction is invariably 4-desacetyl VLB C-3 carboxhydrazide regardless of whether VLB or 4-desacetyl VLB is employed as the starting material. The preparation of compounds of Formula I is carried out with 4-desacetyl VLB C-3 carboxhydrazide, however prepared, as the starting material.

The compounds of this invention are prepared by reacting 4-desacetyl VLB C-3 carboxhydrazide of Formula III

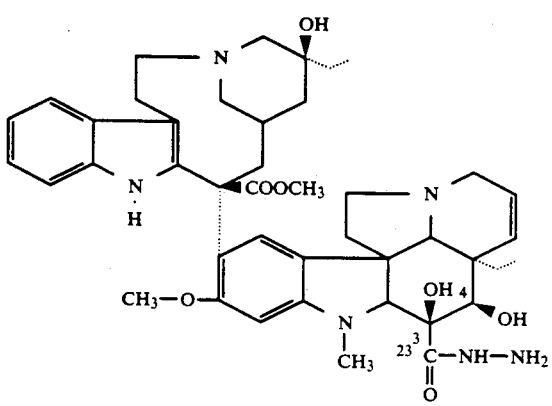

with a keto-acid- or an acid-aldehyde of the general structure

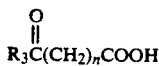

such as succinic semialdehyde, levulinic acid, 4-acetylbutyric acid or 6-ketoheptanoic acid under reflux conditions to form a compound of the structure

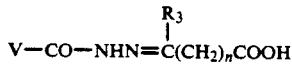

where V represents the vinca alkaloid moiety (all of Formula III except the group attached to C-3), and $R_3$ and n are the same as defined above.

The compounds of the structure IV can be reduced with sodium borohydride or other reducing agents to form compounds of the structure V

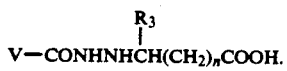

The side chains with an amino acid can be prepared by reacting the keto-acid or acid-aldehyde with an amino acid with a protecting group(X) of the general structure $H_2N(CH_2)_{n'}COX$, and removing the protecting group in order to form a compound of the structure

wherein n' is the same as defined above.

The compounds of structure VI can then be reacted with 4-desacetyl VLB C-3 carboxhydrazide under reflux conditions to form compounds of the structure VII

The compounds of structure VII can be reduced with sodium borohydride or other reducing agents to form compounds of the structure VIII

The conjugates of the invention can be prepared by reacting an immunoglobulin or an immunoglobulin fragment with a hemi-acid comprising a vinca moiety having the

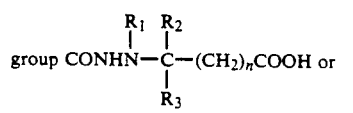

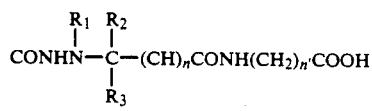

(Y' is OH) attached at the C-3 position. The activating group (Y') is placed on the carboxylic acid by use of a conventional esterification reagent such as an alkyl chloroformate or carbodiimide.

The intermediate containing the

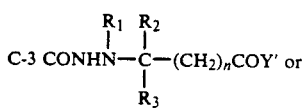

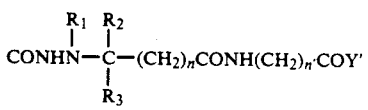

moiety is reacted with the immunoglobulin or immunoglobulin fragment to form the novel conjugates of this invention.

The above Formulas IV, V, VII, and VIII are compounds of Formula I and Formulas IV and VII are also intermediates to compounds of Formula I.

Reaction of an immunoglobulin or an immunoglobulin fragment with a compound of Formula I is preferably carried out in an aqueous medium and at a temperature of from 5° C. to 25° C., for example at room temperature, and at a pH of 7.5 to 9.5, preferably 8.0 to 9.0. The process results in the attachment by covalent linkage of one or more vinca residues at the free amino groups of the immunoglobulin molecule, for example, amino groups derived from lysine residues. The number of residues attached will depend on the concentration of the reactants and the duration of the reaction but the average number is usually for example from 1 to 10.

For example in carrying out the reaction, a solution of the compound of Formula I in a suitable solvent such as dimethylformamide is slowly added dropwise to a buffered solution of immunoglobulin in for example, 0.34M borate buffer at pH 8.6. The conjugate is isolated by gel filtration and stored in saturated ammonium sulphate solution. It is readily brought back into solution by dialysis with a buffer solution, for example, a phosphate buffered saline at pH 7.4, or alternatively it can be stored in a refrigerator at 4° C. or frozen at, for example, −20° C.

Further purification and characterization of the conjugate can be carried out using well known techniques such as affinity chromatography. Protein and drug concentrations are determined by measuring optical densities of conjugate solutions at two wavelengths, for example 270 and 280 nm, and relating the values obtained to those for the free drug and unconjugated immunoglobulin at the same two wavelengths. The efficacy of the conjugate can be estimated by counting the number of viable cells after treatment of a suspension of tumor cells with the conjugate, or from measurements of the uptake of tritiated uridine. Additional evaluation of the conjugates as anti-tumor agents can be made by determining the inhibition or eradication of human derived tumors grown in athymic mice.

The novel compounds and conjugates of the invention are useful in the treatment of cancers and as such are preferably prepared for use in formulations suitable for injection. Cancers refer to leukemias, lymphomas, lung adenocarcinoma, testicular carcinoma, breast carcinoma, osteogenic carcinoma, and colorectal carcinoma. Thus the invention could be used in a pharmaceutical formulation, for example an injectable preparation, comprising a compound or a conjugate of the invention together with a pharmaceutically-acceptable carrier or diluent such as are well known in the art. It is preferably in unit dosage form, each dosage containing for example from 1 to 2 mg of the active ingredient (in terms of the vinca drug moiety).

The novel compounds and conjugates are effective over a wide dosage range and, for example, for the treatment of adult humans, dosages per week will normally fall within the range of 1 to 10 mg/kg (vinca drug moiety), more usually in the range of from 1 to 5 mg/kg. However it will be understood that the amount of compound actually administered will be determined by a physician in the light of the relevant circumstances, including the condition to be treated and the chosen route of administration.

The invention is illustrated but not limited by the following Examples.

In the following Examples, the terms mass spectra, infra-red spectra, retardation factor, thin layer chromatography, high performance liquid chromatography are abbreviated MS, IR, $R_F$, tlc and HPLC, respectively.

In addition, the absorption maxima listed for the IR spectra are only those of interest and not all of the maxima observed.

The HPLC spectra were obtained by using a Waters Varian Prep 500 with two Pre-Pak 500-Silica columns.

The $R_F$ was obtained by tlc utilizing 5×20 cm, 0.2 mm silica gel plates with flourescent indicator. All plates were eluted with ethyl acetate:methanol (1:1). The chromatograms were visualized by short wave ultraviolet spectra (UV) and by a spray reagent $(H_3PO_4\text{-}Ce(NH_4)_2(SO_4)_3)$. Farnsworth, et al., Lloydia, 27(4), 302–314 (1964).

Preparation of Starting Material

4-Desacetyl VLB C-3 carboxhydrazide 65.9 g (0.0725 mole) of vinblastine sulfate was dissolved in 2 L of methanol and 250 g (7.82 mole) of anhydrous hydrazine was added. The reaction mixture was stirred under a nitrogen atmosphere and heated almost to reflux. The reaction was continued for 36 hours and then was allowed to cool. The reaction mixture was filtered and the volatile solvents were removed by evaporation in vacuo, which resulted in a gummy, tan amorphous solid. This product was dissolved in 1 L of methylene chloride and was extracted twice with 500 ml of water. The methylene chloride layer was dried by filtration through anhydrous sodium sulfate and evaporated to dryness in vacuo. This resulted in 49.5 g (0.0648 mole) of crude 4-desacetyl VLB C-3 carboxhydrazide as a tan amorphous powder.

20 g of this crude product was chromatographed (HPLC) on a silica gel column eluted with a linear gradient of 100% ethyl acetate to ethyl acetate:methanol (1:1). The fractions containing the desired product were determined by tlc and combined. The solvents were removed by evaporation in vacuo which yielded 11.68 g (0.0152 mole) of the purified product. This purified product was dissolved in 75 ml of hot methylene chloride and filtered. The product was allowed to crystallize at −20° C. for several hours. The product was filtered and washed with cold methylene chloride and then dried to yield 9.66 g (0.0126 mole) of the desired product as a white crystalline powder.

EXAMPLE 1

4-Desacetyl VLB C-3 $N^2$-(3-carboxy-1-methylpropylidene)carboxhydrazide 7040 mg (9.15 mmole) of 4-desacetyl VLB C-3 carboxhydrazide was dissolved in 200 ml of toluene and approximately 25 ml of methylene chloride. To this solution was added 1.6 g (13.7 mmole) of levulinic acid and 50 g of anhydrous sodium sulfate. The reaction mixture was heated to reflux and stirred vigorously for a period of four hours. The reaction mixture was allowed to cool and was filtered to remove the sodium sulfate. The resulting solution was evaporated to dryness in vacuo. This yielded a white amorphous powder which was used in further reactions.

$R_F = 0.13$.

EXAMPLE 2

4-Desacetyl VLB C-3 $N^2$-(4-carboxy-1-methylbutylidene)carboxhydrazide 1100 mg (1.43 mmole) of 4-desacetyl VLB C-3 carboxhydrazide was dissolved in 25 ml of methylene chloride, and 100 mg (7.7 mmole) of 4-acetylbutyric acid and 250 mg of anhydrous sodium sulfate were added to the reaction mixture. The reaction mixture was sealed under nitrogen and the reaction was allowed to continue at room temperature for a period of three days. The reaction mixture was filtered and the resulting solution was washed with 50 ml of a saturated solution of sodium bicarbonate. The methylene chloride layer was dried by filtration through anhydrous sodium sulfate and the solvent was removed by evaporation in vacuo. The resulting product (930 mg) was an amorphous solid.

IR: $(CHCl_3)$ ∥ (CON)1685 cm$^{-1}$, (COO)1720 and 1735 cm$^{-1}$.

pKa: (66% DMF) 5.1, 6.6, and 7.7.

EXAMPLE 3

4-Desacetyl VLB C-3 N²-(4-carboxy-1-methylbutylidene)carboxhydrazide sulfate salt 110 mg of 4-desacetyl VLB C-3 N²(4-carboxy-1-methylbutylidene)carboxhydrazide was dissolved in 25 ml of absolute ethanol. The initial pH of 8.1 was adjusted to 4.0 by addition of 2% sulfuric acid in absolute ethanol. The reaction solution was evaporated to dryness in vacuo. This resulted in a yield of 30 mg of the desired product as a white amorphous powder.
$R_F = 0.27$.

EXAMPLE 4

4-Desacetyl VLB C-3 N²-(5-carboxy-1-methylpentylidene)carboxhydrazide 4000 mg (5.2 mmole) of 4-desacetyl VLB C-3 carboxhydrazide was dissolved in 250 ml of toluene. To this solution was added 2000 mg (14 mmole) of 6-ketoheptanoic acid and 5000 mg of anhydrous sodium sulfate. The reaction mixture was stirred vigorously and heated to reflux. The reaction was kept under a nitrogen atmosphere for about 20 hours. The reaction was allowed to cool and was filtered. The filtrate was evaporated to dryness in vacuo, yielding 4700 mg of amorphous powder. This powder was dissolved in 50 ml of methylene chloride and further purified by chromatography (HPLC) over a silica gel column eluted with a solvent of ethyl acetate:methanol (1:1). The desired fractions were determined by tlc and combined. The combined fractions were evaporated to dryness in vacuo and yielded 3410 mg of desired product.
MS: m/e 895 (m+H).
pKa: (66% DMF) 5.3, 7.0, and 8.1.

EXAMPLE 5

4-Desacetyl VLB C-3 N²-(5-carboxy-1-methylpentylidene)carboxhydrazide sulfate salt 230 mg of 4-desacetyl VLB C-3 N²-(5-carboxy-1-methylpentylidene)carboxhydrazide was dissolved in 40 ml of absolute ethanol The initial pH of 7.6 was adjusted to 3.9 with the addition of a 2% solution of sulfuric acid in absolute ethanol. The reaction mixture was evaporated to dryness in vacuo. This resulted in a yield of 140 mg of the desired product.
$R_F = 0.34$.

EXAMPLE 6

4-Desacetyl VLB C-3 N²-(5-[(2-carboxyethyl)amino]-1-methyl-5-oxopentylidene)carboxhydrazide A. 6-[((1-Methylpropoxy)carbonyl)oxy]-2-oxohexane 11.7 g (0.09 mole) of 5-ketohexanoic acid was dissolved in 100 ml of dichloromethane and cooled in an ice bath. 20.0 g (0.2 mole) of N-methylmorpholine was added to the reaction mixture which was stirred under nitrogen. 16.4 g (0.12 mole) of isobutyl chloroformate was dissolved in 25 ml of dichloromethane and slowly added to the reaction over 10 minutes. The reaction mixture continued to be stirred at 0° C., under nitrogen for one hour. The reaction mixture was evaporated in vacuo to an oily solid and used in subsequent reactions.

B. 6-[((2-Benzyloxycarbonyl)ethyl)amino]-2,6-dioxohexane

All of the 6-[((1-methylpropoxy)carbonyl)oxy]-2-oxohexane from Example 6A was dissolved in 50 ml of dichloromethane. A solution was prepared of 35.1 g (0.1 mole) of β-alanine benzylester p-toluenesulfonic acid salt and 10 g (0.1 mole) of N-methylmorpholine in 50 ml of dichloromethane. The solution containing the free amine was cooled in an ice bath and slowly over a period of 30 minutes the solution containing the mixed anhydride was added. The reaction was allowed to continue for 16 hours under nitrogen and was slowly warmed to room temperature. The resulting solution was extracted with 50 ml of 1N sodium hydroxide, 1N hydrochloric acid and then water. The resulting dichloromethane layer was dried by filtration through anhydrous sodium sulfate and evaporated to dryness in vacuo. This yielded 20.7 g of the desired title compound as a white solid.
MS: m/e 291 (M+),
Anal: Calculated for $C_{16}H_{21}NO_4$; Theoretical: C, 65.96; H, 7.26; N, 4.81; Found: C, 64.99; H, 8.18; N, 4.58.

C. 6-[(2-Carboxyethyl)amino]-2,6-dioxohexane 20.5 g (0.071 mole) of 6-[((2-benzyloxycarbonyl)ethyl)amino]-2,6-dioxohexane was dissolved in 200 ml of absolute ethanol and 80 g (0.3 mole) of 1,4-cyclohexadiene was added. 5 g of 5% Pd on carbon catalyst was added. The reaction mixture was stirred vigorously under a nitrogen atmosphere and heated to reflux for 16 hours. The reaction mixture was allowed to cool and the catalyst was filtered off. The resulting solution was evaporated to dryness in vacuo which left an oily solid. This solid was dissolved in 100 ml of ethyl acetate and extracted with 50 ml of 1N sodium hydroxide. The basic aqueous solution was made acidic with 1N hydrochloric acid until cloudy and extracted twice with 50 ml of ethyl acetate. The combined ethyl acetate extracts were dried by filtration through anhydrous sodium sulfate and evaporated to an oil which solidified on standing, which resulted in 11.6 g of the desired product.
MS: m/e 202 (m+1).
pKa: 7.1.
Anal: Calculated for $C_9H_{15}NO_4$; Theoretical: C, 53.72; H, 7.51; N, 6.96; Found: C, 56.75; H, 8.04; N, 5.21.

D. 4-Desacetyl VLB C-3 N²-(5-[(2-carboxyethyl)amino]-1-methyl-5-oxopentylidene)carboxhydrazide 4000 mg (5.2 mmole) of 4-desacetyl VLB C-3 carboxhydrazide was dissolved in 100 ml of tetrahydrofuran (THF) and 5000 mg of anhydrous sodium sulfate was added. To this was added 4000 ml (20 mmole) of 6-[(2-carboxyethyl)amino]-2,6-dioxohexane. The reaction was stirred and heated under a nitrogen atmosphere to reflux. After 20 hours the reaction mixture was filtered and evaporated to dryness in vacuo. The compound was further purified by HPLC over a silica gel column eluted with a linear gradient of solvent, beginning with ethyl acetate:methanol (2:1) and ending with 100% methanol. The fractions containing the desired compound were determined by tlc and combined and evaporated to dryness in vacuo which yielded 2100 mg of the desired product.
MS: m/e 973 (m+22, Na ion).

pKa: (66% DMF) 5.1, 6.6, and 7.3.
$R_f = 0.11$.

EXAMPLE 7

4-Desacetyl VLB C-3
$N^2$-(5-[(2-carboxyethyl)amino]-1-methyl-5-oxopentylidene)carboxyhydrazide sulfate salt 94 mg of 4-desacetyl VLB C-3 $N^2$-(5-[(2-carboxyethyl)amino]-1-methyl-5-oxopentylidene)carboxyhydrazide was, dissolved in 15 ml of absolute ethanol. The initial pH of 7.6 was adjusted to 3.5 with 2% sulfuric acid in absolute ethanol. The reaction mixture was evaporated to dryness in vacuo, which yielded 70 mg of the desired product.
$R_F = 0.19$.

EXAMPLE 8

4-Desacetyl VLB C-3
$N^2$-(6-[(2-carboxyethyl)amino]-1-methyl-6-oxohexylidene)carboxyhydrazide A. 7-[((1-Methylpropoxy)carbonyl)oxy]-2-oxoheptane 11.2 g (0.07 mole) of 6-ketoheptanoic acid was dissolved in 100 ml of dichloromethane and 10 g of N-methylmorpholine was added. The reaction mixture was cooled in an ice bath, stirred and kept under a nitrogen atmosphere. 11.6 g (0.085 mole) of isobutyl chloroformate dissolved in 25 ml of dichloromethane was slowly added over a period of 15 minutes. The reaction mixture was allowed to proceed for one hour. The reaction mixture was evaporated to an oily solid and used in subsequent reactions.

B. 7-[((2-Benzyloxycarbonyl)ethyl)amino]-2,7-dioxoheptane 35.1 g (0.1 mole) of β-alanine benzylester p-toluenesulfonic acid salt and 10 g (0.1 mole) of N-methylmorpholine were combined in 100 ml of dichloromethane and cooled in an ice bath. All of the 7-[((1-methylpropoxy)carbonyl)oxy]-2-oxoheptane from Example 8A was dissolved in 25 ml of dichloromethane and was slowly added over a 15 minute period to the reaction mixture. The reaction was allowed to proceed under nitrogen for 16 hours while slowly warming to room temperature. The reaction mixture was extracted with 50 ml of sodium hydroxide, 1N hydrochloric acid and then water. The resulting dichloromethane layer was dried by filtration through anhydrous sodium sulfate and evaporated to dryness. This yielded 14.25 g of the desired product as a white powder.

MS: m/e 305. IR: (CHCl$_3$) 3350, 2958, 1726, 1716, and 1665 cm$^{-1}$.

Anal: Calculated for $C_{17}H_{23}NO_4$; Theoretical: C, 66.87; H, 7.59; N, 4.59; Found C, 66.79; H, 7.80; N, 4.32.

C. 7-[(2-Carboxyethyl)amino]-2,7-dioxoheptane 10.47 g (0.034 mole) of 7-[((2-benzyloxycarbonyl)ethyl)amino]-2,7-dioxoheptane was dissolved in 100 ml of absolute ethanol and 8 g (0.1 mole) of 1,4-cyclohexadiene was added along with 2 g of 5% Pd on carbon. The reaction mixture was stirred under nitrogen and heated to reflux for 16 hours. The reaction was allowed to cool and was filtered to remove the catalyst. The reaction mixture was evaporated to a solid and then dissolved in 300 ml of ethyl acetate. The ethyl acetate solution was extracted with 100 ml of 1N sodium hydroxide. The aqueous solution was acidified with 1N hydrochloric acid until cloudy and extracted twice with ethyl acetate. The combined ethyl acetate extracts were dried by filtration through anhydrous sodium sulfate and evaporated in vacuo to yield 1.05 g of the desired product.

MS: m/e 216 (m+1).

Anal: Calculated for $C_{10}H_{17}NO_4$; Theoretical: C, 55.08; H, 7.96; N, 6.51; Found: C, 54.04; H, 7.58; N, 6.77.

D. 4-Desacetyl VLB C-3
$N^2$-(6-[(2-carboxyethyl)amino]-1-methyl-6-oxohexylidene)carboxyhydrazide 2800 mg (3.6 mmole) of 4-desacetyl VLB C-3 carboxhydrazide was dissolved in 100 ml of tetrahydrofuran and 5000 mg of anhydrous sodium sulfate was added. 1.05 g (4.8 mmole) of 7-[(2-carboxyethyl)amino]-2,7-dioxoheptane was added to the reaction mixture. The reaction was allowed to proceed by heating under a nitrogen atmosphere to reflux for 20 hours. The reaction was filtered and evaporated to dryness in vacuo. The reaction product was further purified by HPLC over a silica gel column eluted with a solvent in a linear gradient of 100% ethyl acetate to ethyl acetate:methanol (1:1). Combining the desired fractions and evaporated them to dryness in vacuo, yielded 1700 mg of desired product.

MS: m/e 987 (m+22, Na ion).
pKa: (66% DMF) 5.0, 6.2, and 7.8.

EXAMPLE 9

4-Desacetyl VLB C-3
$N^2$-(6-[(2-carboxyethyl)amino]-1-methyl-6-oxohexylidene)carboxyhydrazide sulfate salt 95 mg of 4-desacetyl VLB C-3 $N^2$-(6-[(2carboxyethyl)amino]-1-methyl-6-oxohexylidene)carboxyhydrazide was dissolved in 15 ml of absolute ethanol. The initial pH of 8.2 was adjusted to 3.6 with a solution of 2% sulfuric acid in absolute ethanol. The reaction mixture was evaporated to dryness in vacuo, yielding 70 mg of the desired product.
$R_F = 0.12$.

EXAMPLE 10

4-Desacetyl VLB C-3
$N^2$-(3-carboxy-1-methylpropyl)carboxyhydrazide

The resulting product of Example 1, 4-desacetyl VLB C-3 $N^2$-(3-carboxy-1-methylpropylidene)carboxhydrazide, was dissolved in 100 ml of absolute ethanol and a small amount of methylene chloride. The reaction solution was cooled to 0° C. in an ice bath. The reaction solution was placed under a nitrogen atmosphere and stirred, while adding 5000 mg (130 mmole) of sodium borohydride. The reaction was allowed to proceed for 20 hours and was evaporated to dryness in vacuo. The reaction mixture was redissolved in 50 ml of 1N hydrochloric acid and made basic with the addition of a saturated solution of sodium bicarbonate. The product was extracted with 50 ml of methylene chloride. The methylene chloride solution was dried by filtration through anhydrous sodium sulfate and was evaporated to dryness in vacuo. The product was further purified by HPLC on a silica gel column eluted with a linear gradient of 100% ethyl acetate to ethyl acetate:methanol (1:1). This yielded 2500 mg of the desired product.

IR: (CHCl$_3$) || (COO) 1720 and 1740 cm$^{-1}$, (CON) 1660 cm$^{-1}$.

MS: m/e 850 (m—18, loss of H$_2$O).

pKa: (66% DMF) 5.3, 6.9, and 7.9.

EXAMPLE 11

4-Desacetyl VLB C-3 $N^2$-(3-carboxy-1-methylpropyl)carboxyhydrazide sulfate salt 240 mg of 4-desacetyl VLB C-3 $N^2$-(3-carboxy-1-methylpropyl)carboxyhydrazide was dissolved in 25 ml of absolute ethanol along with the addition of a small amount of methanol to help it into solution. The reaction mixture was filtered. The initial pH of 8.0 was adjusted to 4.0 with 2% sulfuric acid in absolute ethanol. The product precipitated out and was evaporated to dryness in vacuo. This resulted in 120 mg of white amorphous powder.
$R_F = 0.22$.

EXAMPLE 12

4-Desacetyl VLB C-3 $N^2$-(5-carboxy-1-methylpentyl)carboxyhydrazide 2000 mg (2.2 mmole) of 4-desacetyl VLB C-3 $N^2$-(5-carboxy-1-methylpentylidene)carboxyhydrazide was dissolved in 60 ml of absolute ethanol and 200 mg (5.2 mmole) of sodium borohydride was added. The reaction was placed under a nitrogen atmosphere, stirred and allowed to react for 20 hours at room temperature. The reaction mixture was evaporated to dryness in vacuo and redissolved in 50 ml of 1N hydrochloric acid. This solution was made basic with saturated sodium bicarbonate reagent and extracted with 50 ml of methylene chloride. The methylene chloride extract was dried by filtration through anhydrous sodium sulfate and evaporated to dryness in vacuo, which resulted in 1470 mg of the desired product.
MS: m/e 896 (m),
$R_F = 0.22$,

EXAMPLE 13

4-Desacetyl VLB C-3 $N^2$-(5-carboxy-1-methylpentyl)carboxyhydrazide sulfate salt 310 mg of 4-desacetyl VLB C-3 $N^2$-(5-carboxy-1methylpentyl)carboxyhydrazide was dissolved in 50 ml of absolute ethanol. The initial pH of 6.8 was adjusted to 4.1 with 2% sulfuric acid in absolute ethanol. The reaction mixture was evaporated to dryness in vacuo, which yielded 210 mg of the desired product as a white amorphous powder.
$R_F = 0.2$,

EXAMPLE 14

4-Desacetyl VLB C-3 $N^2$-(5-[(2-carboxyethyl)amino]-1-methyl-5-oxopentyl)-carboxyhydrazide 600 mg (0.63 mmole) of 4-desacetyl VLB C-3 $N^2$-(5-[(2-carboxyethyl)amino]-1-methyl-5-oxopentylidene)-carboxyhydrazide was dissolved in 100 ml of ethanol and 600 mg (15.4 mmole) of sodium borohydride was added. The reaction was allowed to proceed at room temperature for 20 hours under a nitrogen atmosphere. The reaction mixture was evaporated to dryness and redissolved in 50 ml of 1N hydrochloric acid. The acid solution was made basic with saturated sodium bicarbonate reagent and extracted with 50 ml of methylene chloride. The methylene chloride extract was dried by filtration through anhydrous sodium sulfate and evaporated to dryness in vacuo, which resulted in 200 mg of the desired product.
MS: m/e 976 (M+23, Na ion).
pKa: (66% DMF) 5.7, 6.7, and 7.9.

EXAMPLE 15

4-Desacetyl VLB C-3 $N^2$-(5-[(2-carboxyethyl)amino]1-methyl-5-oxopentyl)-carboxyhydrazide sulfate salt 200 mg of 4-desacetyl VLB C-3 $N^2$-(5-[(2-carboxyethyl)amino]-1-methyl-5-oxopentyl)carboxyhydrazide was dissolved in 40 ml of absolute ethanol The initial pH of 7.5 was adjusted to 3.8 with 2% sulfuric acid in absolute ethanol. The reaction mixture was evaporated to dryness in vacuo, which yielded 200 mg of the desired product as a white amorphous powder.
$R_F = 0.079$.

EXAMPLE 16

4-Desacetyl VLB C-3 $N^2$-(6-[(2-carboxyethyl)amino]-1-methyl-6-oxohexyl)-carboxyhydrazide 1000 mg (1.0 mmole) of 4-desacetyl VLB C-3 $N^2$-(6-[(2-carboxyethyl)amino]-1-methyl-6-oxohexylidene)-carboxyhydrazide was dissolved in 100 ml of ethanol and 600 mg (15.4 mmole) of sodium borohydride was added. The reaction mixture was stirred at room temperature for 20 hours under nitrogen. The reaction mixture was evaporated to dryness and redissolved in 50 ml of 1N hydrochloric acid. The acid solution was made basic with saturated sodium bicarbonate and extracted with 50 ml of methylene chloride. The methylene chloride extract was dried by filtration through anhydrous sodium sulfate and evaporated to dryness This yielded 740 mg of the desired product.
MS: m/e 989 (m+22, Na ion).
$R_F = 0.18$.

EXAMPLE 17

4-Desacetyl VLB C-3 $N^2$-(6-[(2-carboxyethyl)amino]-1-methyl-6-oxohexyl)-carboxyhydrazide sulfate salt 58 mg of 4-desacetyl VLB C-3 $N^2$-(6-[(2-carboxyethyl)amino]-1-methyl-6-oxohexyl)carboxyhydrazide was dissolved in 20 ml of absolute ethanol The initial pH of 8.6 was adjusted to 4.0 with 2% sulfuric acid in absolute ethanol. The reaction mixture was evaporated to dryness in vacuo, which yielded 30 mg of tan amorphous powder.
$R_F = 0.16$.

EXAMPLE 18

4-Desacetyl VLB C-3 $N^2$-(6-((3-[2-methylpropoxy]carbonyl)oxy)-1-methyl-6-oxohexylidene)carboxyhydrazide 100 mg (0.11 mmole) of 4-desacetyl VLB C-3 $N^2$-(5-carboxy-1-methylpentylidene)carboxyhydrazide was dissolved in 50 ml of methylene chloride and 35 mg (0.33 mmole) of N-methylmorpholine was added. The reaction was placed under nitrogen and stirred in an ice bath. After a few minutes, 25 mg (0.17 mmole) of isobutyl chloroformate was added, the reaction was allowed to continue for one hour. The reaction mixture was evaporated to dryness in vacuo, which resulted in a tan amorphous powder which was used immediately in the following Example 19.

EXAMPLE 19

4-Desacetyl VLB C-3 N²-[6-[(2,5-dioxo-1-pyrrolidinyl)oxy]-1-methyl-6-oxohexylidene]carboxhydrazide 4-Desacetyl VLB C-3 N²-(6-(([1-methylpropoxy]carbonyl)oxy)-1-methyl-6-oxohexylidene)carboxhydrazide was redissolved in 50 ml of methylene chloride and placed in a hot water bath so the solvent was at reflux. 50 mg (0.44 mmole) of N-hydroxysuccinimide (NHS) was added and the reaction was stirred under nitrogen at a reflux for one hour. The reaction mixture was evaporated and taken up in 2 ml of methylene chloride and the product precipitated with ether. The solvents were decanted off. This process was repeated three times The final product was dried and used in further reactions.

EXAMPLE 20

4-Desacetyl VLB C-3 N²-(5-((3-[[(2-methylpropoxy)carbonyl]oxy]-3-oxopropyl)amino)-1-methyl-5oxopentylidene)carboxhydrazide 1090 mg (1.14 mmole) of 4-desacetyl VLB C-3 N²-(5-[(2-carboxyethyl)amino]-1-methyl-5-oxopentylidene)-carboxhydrazide was dissolved in 250 ml of methylene chloride and 340 mg (3.4 mmole) of N-methylmorpholine was added. The reaction was placed under nitrogen and stirred in an ice bath. After a few minutes 310 mg (2.3 mmole) of isobutyl chloroformate was added, and the reaction was allowed to continue for one hour. The reaction mixture was evaporated to dryness in vacuo and the product was used immediately in the following Example 21.

EXAMPLE 21

4-Desacetyl VLB C-3 N²-(5-[[3-[(2,5-dioxo-1-pyrrolidinyl)oxy]-3-oxopropyl]amino]-1-methyl-5-oxopentylidene)carboxhydrazide All of the 4-desacetyl VLB C-3N²-(5-((3-[[(2-methylpropoxy)carbonyl]oxy]-3-oxopropyl)amino)1-methyl-5-oxopentylidene)carboxhydrazide from Example 20 was redissolved in 150 ml of methylene chloride and placed in a hot water bath so the solvent was at a reflux. 400 mg (3.4 mmole) of N-hydroxysuccinimide was added and the reaction was stirred under nitrogen at a reflux for one hour. The reaction mixture was evaporated and taken up in 2 ml of methylene chloride and the product precipitated with ether. The solvents were decanted off. This process was repeated three times. The final product was dried and yielded 1.12 g which was used in further reactions.

EXAMPLE 22

4-Desacetyl VLB C-3 N²-(6-[[3-[[(2-methylpropoxy)carbonyl]oxy]-3-oxopropyl]amino]-1-methyl-6-oxohexylidene)carboxhydrazide 200 mg (0.21 mmole) of 4-desacetyl VLB C-3 N²-(6-[(2-carboxyethyl)amino]-1-methyl-6-oxohexylidene)-carboxhydrazide was dissolved in 50 ml of methylene chloride and 110 mg (1.1 mmole) of N-methylmorpholine was added. The reaction was placed under nitrogen and stirred in an ice bath. After a few minutes 70 mg (0.53 mmole) of isobutyl chloroformate was added. The reaction was allowed to continue for one hour. The reaction mixture was evaporated to dryness in vacuo and the product was used immediately in the following Example 23.

EXAMPLE 23

4-Desacetyl VLB C-3 N²-(6-[[3-[(2,5-dioxo-1pyrrolidinyl)oxy]-3-oxopropyl]amino]-1-methyl-6-oxohexylidene)carboxhydrazide All of the 4-desacetyl VLB C-3 N²-(6-[[3-[(2,5-dioxo-1-pyrrolidinyl)oxy]-3-oxopropyl]amino]-1-methyl-6-oxohexylidene)carboxhydrazide from Example 22 was redissolved in 50 ml of methylene chloride and placed 75 mg (0.63 mmole) of N-hydroxysuccinimide was added and the reaction was stirred under nitrogen at a reflux for one hour. The reaction mixture was evaporated and taken up in 2 ml of methylene chloride and the product precipitated with ether. The solvents were decanted off. This process was repeated three times. The final product was dried and used in further reactions.

EXAMPLE 24

4-Desacetyl VLB C-3 N²-(6-[[3-[[(2-methylpropoxy)carbonyl]oxy]-3-oxopropyl]amino]-1-methyl-6-oxohexyl)carboxhydrazide 100 mg (0.11 mmole) of 4-desacetyl VLB C-3 N²-6-[(2-carboxyethyl)amino]-1-methyl-6-oxohexyl)carboxhydrazide was dissolved in 50 ml of methylene chloride and 45 mg (0.44 mmole) of N-methylmorpholine was added. The reaction was placed under nitrogen and stirred in an ice bath. After a few minutes 40 mg (0.27 mmole) of isobutyl chloroformate was added, and the reaction was allowed to continue for one hour. The reaction mixture was evaporated to dryness in vacuo and the product was used immediately in the following Example 25.

EXAMPLE 25

4-Desacetyl VLB C-3 N²-(6-[[3-[(2,5-dioxo-1pyrrolidinyl)oxy]-3-oxopropyl]-amino]-1-methyl-6-oxohexyl)carboxhydrazide All of the 4-desacetyl VLB C-3 N²-(6-[[3-[(2,5-dioxo-1-pyrrolidinyl)oxy]-3-oxopropyl]amino]-1-methyl-6-oxohexyl)carboxhydrazide from Example 24 was redissolved in 50 ml of methylene chloride and placed in a hot water bath so the solvent was at a reflux. 45 mg of N-hydroxysuccinimide was added and the reaction was stirred under nitrogen at a reflux for one hour. The reaction mixture was evaporated and taken up in 2 ml of methylene chloride and the product precipitated with ether. The solvents were decanted off. This process was repeated three times. The final product was dried and used in further reactions.

EXAMPLE 26

4-Desacetyl VLB C-3 N²-(4-methoxy-4-oxobutylidene)carboxhydrazide 512 mg (0.66 mmole) of 4-desacetyl VLB C-3 carboxhydrazide was dissolved in 25 ml of methylene chloride and 500 mg (4.3 mmole) of 4-methoxy-4-oxobutyraldehyde was added. The reaction mixture was stirred and 1000 mg of anhydrous sodium sulfate was added. The reaction was allowed to proceed at room temperature, under nitrogen, for 20 hours. The reaction was filtered and the product precipitated out with hexane. The resulting product was a gummy solid.

EXAMPLE 27

4-Desacetyl VLB C-3 $N^2$-(6-methoxy-1-methyl-6-oxohexylidene)carboxhydrazide A small sample of 4-desacetyl VLB C-3 $N^2$-[6-[(2,5-dioxo-1-pyrrolidinyl)oxy]-1-methyl-6oxohexylidene]carboxhydrazide was dissolved in 10 ml of methanol. After several hours the reaction mixture was evaporated to dryness.
$R_F = 0.62$.

EXAMPLE 28

4-Desacetyl VLB C-3 $N^2$-[5-[(3-methoxy-3-oxopropyl)amino]-1-methyl-5-oxopentylidene]carboxhydrazide 100 mg of 4-desacetyl VLB C-3 $N^2$-(5-[[3-[(2,5-dioxo-1-pyrrolidinyl)oxy]-3-oxopropyl]amino]-1-methyl-5-oxopentylidene)carboxhydrazide was dissolved in 25 ml of methanol for several hours. The reaction mixture was evaporated to dryness yielding a tan amorphous product.
MS: m/e 965 (m).
$R_F = 0.42$.

EXAMPLE 29

4-Desacetyl VLB C-3 $N^2$-(6-[(3-methoxy-3-oxopropyl)amino]-1-methyl-6-oxohexylidene)carboxhydrazide A small sample of 4-desacetyl VLB C-3 $N^2$-(6-[[3-[(2,5-dioxo-1-pyrrolidinyl)oxy]-3-oxopropyl]amino)-1-methyl-6-oxohexylidene)carboxhydrazide was dissolved in 25 ml of methanol, sealed under nitrogen and allowed to react at room temperature for 3 days. The product was recovered by evaporation of the solvent. A tan amorphous solid was recovered.
MS: m/e 979(m).
$R_F = 0.44$.

EXAMPLE 30

4-Desacetyl VLB C-3 $N^2$-(6-[(3-methoxy-3-oxopropyl)amino]-1-methyl-6-oxohexyl)carboxhydrazide A small sample of 4-desacetyl VLB C-3 $N^2$-(6-[[3-[(2,5-dioxo-1-pyrrolidinyl)oxy]-3-oxopropyl]amino]-1-methyl-6-oxyhexyl)carboxhydrazide was dissolved in 25 ml of methanol, sealed under nitrogen and allowed to react at room temperature overnight. The reaction mixture was evaporated and redissolved in 50 ml of methylene chloride. The methylene chloride was washed with 25 ml of water and dried with anhydrous sodium sulfate and then evaporated to dryness. A tan amorphous powder was recovered.
$pK_a$: 5.4 and 7.5.
$R_F = 0.70$.

EXAMPLE 31

Conjugate of antibody 007B with 4-desacetyl VLB C-3 $N^2$-(6-[[3-[(2,5-dioxo-1-pyrrolidinyl)oxy]-3-oxopropyl]amino]-1-methyl-6-oxohexylidene)carboxhydrazide Antibody 007B is produced by a hybridoma which is a subclone derived from the hybridoma producing the antibody KS1/4, which is described by Varki et al., *Cancer Research*, 44, 681–86 (1984). A portion of the antibody was dialyzed into pH 8.6 borate buffer, at a concentration of 18 mg/ml. 170 mg (0.16 mmole) of 4-desacetyl VLB C-3 $N^2$-(6-[[3-[(2,5-dioxo-1-pyrrolidinyl)oxy]-3-oxopropyl]amino]-1-methyl-6-oxohexylidene)carboxhydrazide was dissolved in 2.7 ml of dimethylformamide which was then added dropwise to 600 mg (0.004 mmole) of the antibody in solution The conjugation reaction was stirred for one hour at room temperature and then was centrifuged The supernatant was run over a Sephadex G-25 gel column (Pharmacia, Piscataway, N.J.), eluted with physiological buffered saline at pH 7.4. The eluant was filtered through a 0.2 μm porous membrane and was analyzed by ultraviolet analysis. The product was then concentrated using an Amicon ultracentrifugation system (Amicon, Danvers, Mass.) with a 30,000 MW cut off. After eight hours the product was reevaluated by ultraviolet analysis 524 mg of the conjugate was obtained at a concentration of 20.2 mg/ml and at a conjugation ratio of 1.8 moles of vinca drug per mole of antibody.

EXAMPLE 32

Conjugate of antibody 007B with 4-desacetyl VLB C-3 $N^2$-(6-[[3-[(2,5-dioxo-1-pyrrolidinyl)oxy]-3-oxopropyl]amino]-1-methyl-6-oxohexyl)carboxhydrazide A portion of the antibody was dialyzed into pH 8.6 borate buffer, at a concentration of 17.8 mg/ml. 170 mg (0.16 mmole) of 4-desacetyl VLB C-3 $N^2$-(6-[[3-[(2,5-dioxo-1-pyrrolidinyl)oxy]-3-oxopropyl]amine]-1-methyl-6-oxohexyl)carboxhydrazide was dissolved in a 2.7 ml of dimethylformamide which was then added dropwise to 600 mg (0.004 mmole) of the antibody in solution. The conjugation reaction was stirred for one hour at room temperature and then was centrifuged. The supernatant was run over a Sephadex G-25 gel column (Pharmacia, Piscataway, N.J.), eluted with physiological buffered saline at pH 7.4. The eluant was filtered through a 0.2 μm porous membrane and was analyzed by ultraviolet analysis. The product was then concentrated using an Amicon ultracentrifugation system (Amicon, Danvers, Mass.) with a 30,000 MW cut off. After twelve hours the product was reevaluated by ultraviolet analysis. It was noted that some product had gummed up on the filter which resulted in a lower yield. 215 mg of the conjugate was obtained at a concentration of 18.2 mg/ml and at a conjugation ratio of 2.0 moles of vinca drug per mole of antibody.

EXAMPLE 33

Conjugate of antibody 007B with 4-desacetyl VLB C-3 $N^2$-(5-[[3-[(2,5-dioxo-1-pyrrolidinyl)oxy]-3-oxopropyl]amino]-1-methyl-5-oxopentylidene)carboxhydrazide A portion of the antibody was dialyzed into pH 8.6 borate buffer at a concentration of 18.8 mg/ml. 83.34 mg (0.08 mmole) of 4-desacetyl VLB C-3 $N^2$-(5-[[3-[(2,5-dioxo-1-pyrrolidinyl)oxy]-3-oxopropyl]amino]-1-methyl-5-oxopentylidene)carboxhydrazide was dissolved in 2.55 ml of dimethylformamide which was then added dropwise to 600 mg (0.004 mmole) of the antibody in solution. The conjugation reaction was stirred for one hour at room temperature and then centrifuged. The supernatant was run over a Sephadex G-25 gel column (Pharmacia, Piscataway, N.J.), eluted with physiological buffered saline at pH 7.4. The eluant was filtered through a 0.2 μm porous membrane and was analyzed by ultraviolet analysis. The product was then concentrated using an Amicon ultra-centrifugation system (Amicon, Danvers, Mass.) with a 30,000 MW cut off. After four hours the product was reevaluated by ultraviolet analysis. The product was then split into 100 mg lots and lyophilized. 556.8 mg of the conjugate was obtained at a concentration of 11.6 mg/ml and at a conjugation ratio of 4.1 moles of vinca drug per mole of antibody The compounds of the present invention inhibit the growth of human leukemic cells (CCRF-CEM cell line). The CEM cells were grown in RPMI 1640 media (MA Bioproducts) at 37° C. in humidified atmospheric conditions of 95% air and 5% $CO_2$. The cells were grown in static suspension and maintained in log growth phase at a concentration of $3-7 \times 10^5$ cells/ml. The cells were dispersed in wells at a concentration of $4.8 \times 10^4$/well. The drug was dissolved in dimethyl sulfoxide and was added at different dilutions to the cluster plates (wells). The cluster plates were incubated at 37° C. for 72 hours. After 72 hours the wells were read using a ZBI Coulter particle counter. Table 3 below gives the results of such testing of several compounds represented by Formula I above. In the table, Column 1 gives the name of the compound and Column 2 gives the $IC_{50}$ (concentration giving 50% growth inhibition) in µg/ml.

TABLE 3

| CCRF - CEM Cytotoxicity Assay | |
|---|---|
| Compound Name | $IC_{50}$ µg/ml |
| 4-Desacetyl VLB C-3 $N^2$-(3-carboxy-1-methyl-propyl)carboxhydrazide sulfate salt | 0.1 |
| 4-Desacetyl VLB C-3 $N^2$-(5-carboxy-1-methyl-pentylidene)carboxhydrazide sulfate salt | 0.2 |
| 4-Desacetyl VLB C-3 $N^2$-(5-carboxy-1-methyl-pentyl)carboxhydrazide sulfate salt | 0.4 |
| 4-Desacetyl VLB C-3 $N^2$-(1-methyl-5-oxo-5-[(2-carboxyethyl)amino]pentylidene)carbox-hydrazide sulfate salt | 0.095 |
| 4-Desacetyl VLB C-3 $N^2$-(1-methyl-5-oxo-5-[(2-carboxyethyl)amino]pentyl)carboxhydrazide sulfate salt | 0.046 |
| 4-Desacetyl VLB C-3 $N^2$-(1-methyl-6-oxo-6-[(2-carboxyethyl)amino]hexylidene)carbox-hydrazide sulfate salt | 0.068 |
| 4-Desacetyl VLB C-3 $N^2$-(1-methyl-6-oxo-6-[(2-carboxyethyl)amino]hexyl)carboxhydrazide sulfate salt | 0.039 |

The compounds and conjugates of the present invention inhibit the growth of human lung adenocarcinoma cells (P3/UCLA cell line). The CEM cells were harvested with trypsin-EDTA and then brought up in DMEM Complete and the resulting suspension was adjusted to $6.67 \times 10^4$ cells/ml DMEM Complete consisted of 500 ml of Dulbeceo's Modified Eagle Medium (Gibco 380-2430), 10% dialyzed Fetal Bovine Serium (Gibco 220-6300 AJ), 1.0% L-Glutamine (100x conc) (Gibco 320-5030), and 0.1% Gentamicin Sulfate (50 mg/ml) (Gibco 600-5750). The cells were dispersed into wells at a volume of 150 µl. The drug was dissolved and added at different dilutions to the plate. The plate was incubated at 37° C. for 5 days. After 5 days the plates were stained with Giemsa solution (Fisher SG28-100) and read. Table 4 below gives the results of such testing of compounds represented by Formulae I and II above. In the table, Column 1 gives the name of the compound and Column 2 gives the $IC_{50}$ (concentration giving 50% growth inhibition) in µg/ml. Where the compound in Column 1 is a conjugate the $IC_{50}$ in Column 2 is expressed in µg/ml of the vinca content.

TABLE 4

| P3/UCLA - GIEMSA ASSAY | |
|---|---|
| Compound Name | $IC_{50}$ µg/ml |
| 4-Desacetyl VLB C-3 $N^2$-(6-[(2-carboxyethyl)amino]-1-methyl-6-oxohexyl)carboxhydrazide sulfate salt | 0.217 |
| 4-Desacetyl VLB C-3 $N^2$-(6-[(2-carboxyethyl)amino]-1-methyl-6-oxohexylidene)carboxhydrazide sulfate salt | 0.043 |
| Conjugate of antibody 007B with 4-desacetyl VLB C-3 $N^2$-(6-[[3-[(2,5-dioxo-1-pyrrolidinyl)oxy]-3-oxopropyl]amino]-1-methyl-6-oxohexyl)carboxhydrazide | 0.042 |
| Conjugate of antibody 007B with 4-desacetyl VLB C-3 $N^2$-(6-[[3-[(2,5-dioxo-1-pyrrolidinyl)oxy]-3-oxopropyl]amino]-1-methyl-6-oxohexylidene)carboxhydrazide | 0.007 |
| Conjugate of antibody 007B with 4-desacetyl VLB C-3 $N^2$-(5-[[3-[(2,5-dioxo-1-pyrrolidinyl)oxy]-3-oxopropyl]amino]-1-methyl-5-oxopentylidene)carboxhydrazide | 0.003 |

The compounds were tested in vivo against xenografts of P3/UCLA lung adenocarcinoma in female nude mice. The test was begun by implanting each mouse with $10^7$ P3/UCLA tumor cells, subcutaneously. On each of days 2, 5, and 8 after implantation, each mouse was injected with a conjugate or a compound in physiological buffered saline. Control mice were injected with saline only. The doses of conjugate or of vinca intermediate (based on vinca hydrazide content) are indicated below. The size of the tumors induced by implantation was measured on days 14, 21, and 28 after implantation. Each treatment group consisted of five mice. The 28-day results are reported below.

TABLE 5

| Compound | Dose (mg/kg) | % Inhibition |
|---|---|---|
| Conjugate of antibody 007B with 4-desacetyl VLB C-3 $N^2$-(6-[[3-[(2,5-dioxo-1-pyrrolidinyl)oxy]-3-oxopropyl]amino]-1-methyl-6-oxohexyl)carboxhydrazide | 2.00 | 65 |
| | 1.00 | 51 |
| | 0.50 | 5 |
| Conjugate of antibody 007B with 4-desacetyl VLB C-3 $N^2$-(6-[[3-[(2,5-dioxo-1-pyrrolidinyl)oxy]-3-oxopropyl]amino]-1-methyl-6-oxohexylidene)carboxhydrazide | 2.00 | Toxic |
| | 1.00 | Toxic |
| | 0.50 | 95 |
| 4-Desacetyl VLB C-3 $N^2$-(6-[(2-carboxyethyl)-amino]-1-methyl-6-oxohexyl)carboxhydrazide sulfate salt | 2.00 | 39 |
| | 1.00 | 20 |
| 4-Desacetyl VLB C-3 $N^2$-(6-[(2-carboxyethyl)-amino]-1-methyl-6-oxohexylidene)carboxhydrazide sulfate salt | 2.00 | 35 |
| | 1.00 | 43 |
| Conjugate of antibody 007B with 4-desacetyl VLB C-3 $N^2$-(5-[[3-[(2,5-dioxo-1-pyrrolidinyl)-oxy]-3-oxopropyl]amino]-1-methyl-5- | 1.00 | 96 |
| | 0.50 | 95 |
| | 0.25 | 66 |

TABLE 5-continued

| Compound | Dose (mg/kg) | % Inhibition |
|---|---|---|
| oxopentylidene)carboxhydrazide | | |

I claim:

1. A compound of the formula

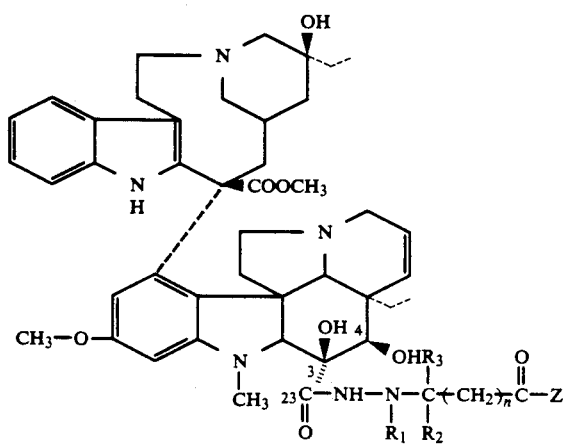

wherein $R_1$ is hydrogen or taken together with $R_2$ to form a direct bond;

$R_2$ is hydrogen or taken together with $R_1$ to form a direct bond;

$R_3$ is hydrogen or methyl;

n is 2–4;

Z is Z' or Z'' wherein Z' is hydroxy, $C_1$–$C_3$ alkoxy, or a carboxylic acid activating group;

Z'' is $-NH(CH_2)_{n'}CO-Z'$;

n' is 1–3;

or a pharmaceutically acceptable salt thereof.

2. A compound of claim 1 wherein $R_1$ is taken together with $R_2$ to form a direct bond.

3. A compound of claim 2 wherein $R_3$ is methyl.

4. A compound of claim 3 wherein Z is Z'.

5. A compound of claim 4 wherein Z' is hydroxy.

6. A compound of claim 3 wherein Z is Z''.

7. A compound of claim 6 wherein Z' is hydroxy.

8. A compound of claim 1 wherein $R_1$ and $R_2$ are hydrogen.

9. A compound of claim 8 wherein $R_3$ is methyl.

10. A compound of claim 9 wherein Z is Z'.

11. A compound of claim 10 wherein Z' is hydroxy.

12. A compound of claim 9 wherein Z' is Z''.

13. A compound of claim 12 wherein Z' is hydroxy.

14. A compound of claim 4 wherein Z' is succinimidoxy.

15. A compound of claim 6 wherein Z' is succinimidoxy.

16. A compound of claim 9 wherein Z' is succinimidoxy.

17. A compound of claim 12 wherein Z' is succinimidoxy.

18. A pharmaceutical composition comprising an effective amount of a compound of claim 1 and a parenterally-administrable medium.

* * * * *